(12) United States Patent
Zhu et al.

(10) Patent No.: US 11,401,561 B2
(45) Date of Patent: Aug. 2, 2022

(54) PRIMER COMPOSITION FOR ANALYZING INTESTINAL FLORA AND APPLICATION THEREOF

(71) Applicant: SUZHOU PRECISION GENE CO. LTD, Jiangsu (CN)

(72) Inventors: Yongliang Zhu, Suzhou (CN); Yanzhao Mu, Suzhou (CN)

(73) Assignee: SUZHOU PRECISION GENE CO. LTD., Jiangsu (CN)

( * ) Notice: Subject to any disclaimer, the term of this patent is extended or adjusted under 35 U.S.C. 154(b) by 71 days.

(21) Appl. No.: 16/611,279

(22) PCT Filed: Dec. 31, 2017

(86) PCT No.: PCT/CN2017/120443
§ 371 (c)(1),
(2) Date: Nov. 6, 2019

(87) PCT Pub. No.: WO2019/114049
PCT Pub. Date: Jun. 20, 2019

(65) Prior Publication Data
US 2020/0165664 A1 May 28, 2020

(30) Foreign Application Priority Data
Dec. 12, 2017 (CN) .......... 201711317948.X (51) Int. Cl.
| | | |
|---|---|---|
| *C12P 19/34* | (2006.01) | |
| *C12Q 1/689* | (2018.01) | |
| *C12N 15/10* | (2006.01) | |
| *C12Q 1/6869* | (2018.01) | |
| *C12Q 1/6886* | (2018.01) | |
| *G01N 1/38* | (2006.01) | |

(52) U.S. Cl.
CPC ......... *C12Q 1/689* (2013.01); *C12N 15/1013* (2013.01); *C12N 15/1093* (2013.01); *C12Q 1/6869* (2013.01); *C12Q 1/6886* (2013.01); *G01N 1/38* (2013.01)

(58) Field of Classification Search
CPC .... C12Q 1/689; C12Q 1/6869; C12Q 1/6886; C12N 15/1093
See application file for complete search history.

(56) References Cited

U.S. PATENT DOCUMENTS

| | | | |
|---|---|---|---|
| 2014/0107092 A1 | 4/2014 | Meyerson et al. | |
| 2015/0232929 A1* | 8/2015 | Stephens | C12Q 1/6853 506/4 |
| 2015/0322492 A1 | 11/2015 | Huang et al. | |
| 2020/0011873 A1* | 1/2020 | Desantis | G01N 33/57407 |

FOREIGN PATENT DOCUMENTS

| | | |
|---|---|---|
| CN | 105189748 A | 12/2015 |
| CN | 105506063 A | 4/2016 |
| CN | 105937053 A | 9/2016 |
| CN | 106497926 A | 3/2017 |
| CN | 107058490 A | 8/2017 |
| WO | 2012170478 A2 | 12/2012 |
| WO | 2015097006 A1 | 7/2015 |
| WO | 2016118719 A1 | 7/2016 |

OTHER PUBLICATIONS

International Search Report issued in PCT/CN2017/120443 dated Sep. 18, 2018.
Wu, et al.: "Comparison of the fecal microbiota of dholes high-throughput Illumina sequencing of the V3-V4 region of the 16S rRNA gene", Appl. Microbiol. Biotechnol. 100 (2016), pp. 3577-3586.

* cited by examiner

*Primary Examiner* — Kenneth R Horlick
(74) *Attorney, Agent, or Firm* — Norton Rose Fulbright US LLP; James R. Crawford (57) ABSTRACT

The present invention provides a primer composition for analyzing intestinal flora, a detection kit composed thereof, and an application of the same. The present invention employs two-step amplification to obtain a sequencing library, and the primer composition comprises a random base.

12 Claims, 2 Drawing Sheets
Specification includes a Sequence Listing.

PRIMER COMPOSITION FOR ANALYZING INTESTINAL FLORA AND APPLICATION THEREOF

This application is a 371 of International Patent Application No. PCT/CN2017/120443 filed on Dec. 31, 2017, and claims priority form Chinese Patent Application No. 201711317948.X filed on Dec. 12, 2017, each of which is incorporated herein by reference in its entirety.

TECHNICAL FIELD

The present application belongs to the field of molecular biology, and relates to a primer composition for analyzing intestinal flora and an application thereof, in particular to a primer composition for analyzing and classifying intestinal flora by constructing a library through two rounds of PCR, a detection kit comprising the same, and an application thereof.

BACKGROUND

The numerous and diverse microbial communities in the gastrointestinal tract of animals have attracted more and more attention and become a research hotspot as they are closely related to the feeding habits, immune function of the body, diseases and health conditions of the animal. However, studies on gastrointestinal microbial communities by using traditional methods involving destructive gastrointestinal sample collection are greatly restricted. In addition, such destructive gastrointestinal sample collection is not desirable for wild protected animals. Therefore, animal feces are generally used as research samples in many studies.

The scientists have also found that there are many differences in the intestinal microorganisms of human populations from different countries, wherein the most significant difference is the degree of microbial diversity. For example, the gut microbiomes of Indians and Malawians are more diverse than those of Americans. There is a view that the higher the degree of microbial diversity, the healthier the human body. The study has also found that although many differences are observed in the gut microbiomes of geographically distinct populations, there are striking similarities among them. For example, the microbiomes in infants from the three different countries have a common formation pattern, that is, infants need 6-9 months to get the first group of 6-700 bacteria, and then several years to get adult microbiomes. The study has also found a very interesting phenomenon, that is, the composition of the gut microbiome changes with age, and this change is precisely adapted to the needs of the human body at different ages.

Studies on intestinal microorganisms have generally gone through three phases i.e., culture-dependent methods, culture-independent traditional molecular biology methods, and sequencing-based high-throughput omics methods.

By comparing the characteristics and applications of the research methods in the 3 phases, one can find that the culture-dependent method can obtain corresponding strains while identifying them, which is convenient for subsequent research. However, the culture itself is a time- and energy-consuming method, and intestinal microorganisms are mainly anaerobic and facultative anaerobic bacteria which are more difficult to cultivate. In addition, the proportion of the bacteria varies during the culture, which causes bottlenecks in its application. The culture-independent traditional molecular biology method can extract directly gut microbial genome from the sample without culture, and the genome can be isolated, identified and quantified by molecular biological means, so that the results can accurately reflect the composition and true proportion of the high-abundance bacteria in gut.

However, traditional molecular biology methods have defects such as low throughput. Targeted methods such as real-time quantitative PCR can only study a species or a class of intestinal microorganisms at a time, and non-targeting methods such as denaturing gradient gel electrophoresis (DGGE) which is the most commonly used is limited by sensitivity and can only be used to study the intestinal microorganisms with a high abundance. The composition of microbial communities is complex, and each bacteria may form a complex network of interactions with other bacteria, and low-abundance strains also play an important role. Therefore, the results obtained by traditional molecular biology research are always one-sided.

16SrDNA is referred as a "molecular clock" in bacterial taxonomy research due to its high diversity among species. It has 9 variable regions and 10 conserved regions in a spaced arrangement. The variable regions vary from bacteria to bacteria and the degree of variation is closely related to the phylogeny of bacteria. Therefore, the taxonomic characteristics of each bacterium can be obtained by analyzing the sequences of the variable regions.

CN 105937053 A discloses a method for establishing a gene library of fecal flora based on high-throughput gene sequencing, which employs a "nested PCR" method for enrichment amplification on 16S rDNA, so as to maximally reduce the genome pollution caused by host and food residue genome. In addition, V3 and V6 are combined for specific amplification and massive parallel sequencing to obtain a sequence database of the target gene of the flora. CN 107058490 A discloses a method for analyzing the diversity and differences of intestinal and oral florae based on a next-generation high-throughput sequencing technology, which uses the Illumina MiSeq® (commercially available from Illumina, Inc., San Diego, Calif.) sequencing system for sequencing to analyze the composition and function of the flora. However, the coverage of the constructed library is not high enough and the detection sensitivity is low.

Based on the above problems, how to design primers that can cover the microorganisms in the sample as completely as possible and improve the specificity and sensitivity of detection has become an urgent problem to be solved.

SUMMARY OF THE INVENTION

In view of the deficiencies in the prior art, the present application provides a primer composition for analyzing intestinal flora and an application thereof. The sequencing library, which is obtained by two-step amplification using the primer composition of the present application comprising random bases, has increased complexity, reduced proportion of phix, higher sequencing quality and improved coverage.

In a first aspect, the present application provides a primer composition for analyzing intestinal flora comprising:

a first set of primers, which comprises a first forward primer and a first reverse primer, wherein the first forward primer includes the following four consecutive portions from 5'- to 3'-end: a first universal sequencing primer, a 2-bp random base sequence, a linker sequence and an intestinal flora 16S rRNA V3-V4 region-specific forward primer; the first reverse primer includes the following four consecutive portions from 5'- to 3'-end: a second universal sequencing primer, a 2-bp random base sequence, a linker sequence and an intestinal flora 16S rRNA V3-V4 region-specific reverse primer;

a second set of primers, which comprises a second forward primer and a second reverse primer, wherein the second forward primer includes the following three consecutive portions from 5'- to 3'-end: a P5-end adaptor sequence, a first tag sequence and partial sequence of the first universal sequencing primer; the second reverse primer includes the following three consecutive portions from 5'- to 3'-end: a P7-end adaptor sequence, a second tag sequence and partial sequence of the second universal sequencing primer.

In the present application, the inventors have found that, by obtaining a sequencing library through two-step amplification, the V3-V4 site-specific degenerate primers comprised in the first set of primers improve the coverage of the amplified fragments, the detection specificity and sensitivity, and more abundant microbiome information can be obtained in combination with data analysis. In addition, the 2-bp random bases comprised in the first set of primers increase the complexity of sequences in the library, reduce the proportion of phix, and ensure higher sequencing quality. The 2-bp Linker sequences that are also comprised in the first set of primers and are not homologous to the 16S genomic sequence can reduce PCR amplification bias. The dual index (tag) design comprised in the second set of primers can mix more samples to a greater extent.

According to the present application, the first universal sequencing primer and the second universal sequencing primer are independently selected from universal sequencing primers that are suitable for any one of next-generation sequencing platforms. Universal sequencing primers suitable for the illumina platform are used in the present application.

According to the present application, the linker sequence has a length of 2-5 bp, such as 2 bp, 3 bp, 4 bp or 5 bp, preferably 2 bp.

According to the present application, the first forward primer has the nucleic acid sequence as shown in SEQ ID NO. 1, and the first reverse primer has the nucleic acid sequence as shown in SEQ ID NO. 2. The nucleic acid sequences are listed as follows.

The first forward primer (SEQ ID NO. 1):
TCGTCGGCAGCGTCAGATGTGTATAAGAGACAG<u>NN</u>TGCCTACGGRRBG

CASCAGKVRVGAAT;

The first reverse primer (SEQ ID NO. 2):
GTCTCGTGGGCTCGGAGATGTGTATAAGAGACAG<u>NN</u>GGGGACTACNV

GGGTWTCTAATCC;

wherein N represents any one of bases A\T\G\C.

According to the present application, the P5-end adaptor sequence has the nucleic acid sequence as shown in SEQ ID NO. 3-12 which are listed as follows.

| | Sequence | Adaptor name |
|---|---|---|
| SEQ ID NO. 3 | CTCTCTAT | S502 |
| SEQ ID NO. 4 | TATCCTCT | S503 |
| SEQ ID NO. 5 | GTAAGGAG | S505 |
| SEQ ID NO. 6 | ACTGCATA | S506 |
| SEQ ID NO. 7 | AAGGAGTA | S507 |
| SEQ ID NO. 8 | CTAAGCCT | S508 |
| SEQ ID NO. 9 | CGTCTAAT | S510 |
| SEQ ID NO. 10 | TCTCTCCG | S511 |
| SEQ ID NO. 11 | TCGACTAG | S513 |
| SEQ ID NO. 12 | TTCTAGCT | S515 |

According to the present application, the P7-end adaptor sequence has the nucleic acid sequence as shown in SEQ ID NO. 13-22 which are listed as follows.

| | Sequence | Adaptor name |
|---|---|---|
| SEQ ID NO. 13 | TCGCCTTA | N701 |
| SEQ ID NO. 14 | CTAGTACG | N702 |
| SEQ ID NO. 15 | TTCTGCCT | N703 |
| SEQ ID NO. 16 | GCTCAGGA | N704 |
| SEQ ID NO. 17 | AGGAGTCC | N705 |
| SEQ ID NO. 18 | CATGCCTA | N706 |
| SEQ ID NO. 19 | GTAGAGAG | N707 |
| SEQ ID NO. 20 | CAGCCTCG | N710 |
| SEQ ID NO. 21 | TGCCTCTT | N711 |
| SEQ ID NO. 22 | TCCTCTAC | N712 |

According to the present application, the first tag sequence of the second forward primer is as shown in SEQ ID NO. 23 which is listed as follows.

The first tag sequence (SEQ ID NO. 23):
AATGATACGGCGACCACCGAGATCTACAC.

According to the present application, the partial sequence of the first universal sequencing primer of the second forward primer is as shown in SEQ ID NO. 24 which is listed as follows.

The partial sequence of the first universal sequencing primer (SEQ ID NO. 24): TCGTCGGCAGCGTC.

According to the present application, the tag sequence of the second reverse primer is as shown in SEQ ID NO. 25 which is listed as follows.

The second tag sequence (SEQ ID NO. 25):
CAAGCAGAAGACGGCATACGAGAT.

According to the present application, the partial sequence of the second universal sequencing primer of the second reverse primer is as shown in SEQ ID NO. 26 which is listed as follows.

The partial sequence of the second universal sequencing primer (SEQ ID NO. 26): GTCTCGTGGGCTCGG.

In the present application, the second forward primer is obtained by combining the first tag sequence as shown in SEQ ID NO. 23 + the P5 adaptor + the partial sequence of the first universal sequencing primer as shown in SEQ ID NO. 24. For example, the second forward primer may be AATGATACGGCGACCACCGAGATCTACAC-CTCTC-TAT-TCGTCGGCAGCGTC. The second reverse primer is obtained by combining the second tag sequence as shown in SEQ ID NO. 25 + the P7 adaptor + the partial sequence of the second universal sequencing primer as shown in SEQ ID NO. 26. For example, the second reverse primer may be CAAGCAGAAGACGGCATACGAGAT-TCGCCTTA-GTCTCGTGGGCTCGG.

In a second aspect, the present application provides a kit for analyzing intestinal flora comprising the primer composition as described in the first aspect.

In a third aspect, the present application provides a method for analyzing intestinal flora by using the primer composition as described in the first aspect, which comprises the steps of (1) extraction of genomic DNA from a sample;
(2) construction of an amplicon library: performing two rounds of PCR amplification to construct a high-throughput sequencing library, wherein the first set of primers is used in the first round of PCR amplification and the second set of primers is used in the second round of PCR amplification;
(3) data analysis.

According to the present application, the sample is derived from any one of the group consisting of feces, soil, urine and oral cells, or a combination of at least two thereof, preferably derived from feces.

According to the present application, the extraction of genomic DNA from a sample as described in step (1) comprises the specific steps of:

(1') mixing the sample with a lysis buffer, and then resuspending;
(2') adding a remover into the resuspended sample obtained in step (1'), mixing and centrifuging;
(3') adding a binding buffer into the centrifuged sample obtained in step (2') and mixing, adding the mixture into an adsorption column, centrifuging, rinsing, adding 75% absolute ethanol, and centrifuging;
(4') adding an eluent into the centrifuged sample obtained in step (3') and centrifuging to obtain the genomic DNA.

According to the present application, the lysis buffer as described in step (1') comprises a Tris-Cl buffer, Tween-40® (polyoxyethylene sorbitan monopalmitate, a nonionic surfactant available from Croda Americas LLC), EDTA and SDS.

Preferably, the molar concentration of the Tris-Cl buffer is 0.5-2 M, such as 0.5M, 0.6 M, 0.7 M, 0.8 M, 0.9 M, 1 M, 1.1 M, 1.2 M, 1.3 M, 1.4 M, 1.5 M, 1.6 M, 1.8 M or 2 M, preferably 0.8-1.2M.

Preferably, the volume fraction of the Tween-40® is 8-15%, such as 8%, 9%, 10%, 11%, 12%, 13%, 14% or 15%, preferably 10-13%.

Preferably, the molar concentration of the EDTA is 0.1-1 M, such as 0.1 M, 0.2 M, 0.3 M, 0.4 M, 0.5 M, 0.6 M, 0.7 M, 0.8 M, 0.9 M or 1 M, preferably 0.1-0.5M.

Preferably, the volume fraction of the SDS is 5-15%, such as 5%, 6%, 7%, 8%, 9%, 10%, 11%, 12%, 13%, 14% or 15%, preferably 8-12%.

According to the present application, the remover as described in step (2') comprises $Al_2(SO_4)_3$, CTAB and NaCl.

Preferably, the molar concentration of the $Al_2(SO_4)_3$ is 0.5-2 M, such as 0.5 M, 0.6 M, 0.7 M, 0.8 M, 0.9 M, 1 M, 1.2 M, 1.3 M, 1.5 M, 1.6 M, 1.7 M, 1.8 M, 1.9 M or 2 M, preferably 0.8-1.2M.

Preferably, the mass concentration of the CTAB is 200-300 g/L, such as 200 g/L, 210 g/L, 220 g/L, 230 g/L, 250 g/L, 260 g/L, 270 g/L, 280 g/L, 290 g/L or 300 g/L, preferably 230-260 g/L.

Preferably, the molar concentration of the NaCl is 0.8-2 M, such as 0.8 M, 0.9 M, 1 M, 1.2 M, 1.3 M, 1.5 M, 1.6 M, 1.7 M, 1.8 M, 1.9 M or 2 M, preferably 1.2-1.8 M.

In the present application, the inventors have found that the addition of the Tween-40® improves the efficiency of sample lysis. Extraction of a single sample can be completed in 45 minutes with an ordinary vortexer without the need of a specific oscillator, which is efficient and convenient. The addition of $Al_2(SO_4)_3$ can effectively adsorb the corrosive substance in the sample. The CTAB has a certain ability to adsorb the corrosion substance, and, at a high salt concentration, can effectively remove the polysaccharide in the sample. The DNA extracted in cooperation with the three reagents has a high purity and can be directly used in subsequent molecular experiments.

According to the present application, the conditions for the first round of PCR as described in step (2) are: pre-denaturation at 93-96° C. for 1-5 min; 25-35 cycles of pre-denaturation at 93-96° C. for 20-40 s, 50-55° C. for 20-40 s, and 70-75° C. for 20-40 s; and extension at 70-75° C. for 3-6 min.

Preferably, the conditions for the first round of PCR as described in step (2) are: pre-denaturation at 95° C. for 3 min; 28 cycles of pre-denaturation at 95° C. for 30 s, 53° C. for 30 s, and 72° C. for 30 s; and extension at 72° C. for 5 min.

According to the present application, the conditions for the second round of PCR as described in step (2) are: pre-denaturation at 93-96° C. for 1-5 min; 6-12 cycles of pre-denaturation at 93-96° C. for 20-40 s, 54-58° C. for 20-40 s, and 70-75° C. for 20-40 s; and extension at 70-7° C. for 3-6 min.

Preferably, the conditions for the second round of PCR as described in step (2) are: pre-denaturation at 95° C. for 3 min; 8 cycles of pre-denaturation at 95° C. for 30 s, extension at 55.5° C. for 30 s, and 72° C. for 30 s; 1 cycle of 72° C. for 5 min.

According to the present application, a purification step is further included after step (1), preferably the purification is performed by using magnetic beads.

According to the present application, the volume ratio of the magnetic beads to the amplification product is (0.4-0.7):1, such as 0.4:1, 0.5:1, 0.6:1 or 0.7:1, preferably 0.5:1.

According to the present application, the data analysis as described in step (3) is performed by using an Illumina MiSeq® sequencer for sequencing analysis.

According to the present application, the sequencing analysis specifically comprises the steps of: sequencing with an Illumina MiSeq® sequencer to obtain sequencing reads differentiated by tags, assembling according to the overlap relationship of the reads to obtain full-length sequences of the high variable region V3-V4, and then classifying and analyzing the full-length sequences to obtain a classification of the microbial population.

According to the present application, the step of classifying and analyzing of the full-length sequences specifically includes the steps of calculating the diversity of the full-length sequences, performing operational taxonomy unit (OTU) classification according to the sequence diversity, assigning the full-length sequences to OTUs, then aligning the full-length sequences in each OTU classification to the V6 database of 16S rRNA and annotating the OTUs at species level by using the alignment results according to the mode principle.

In a fourth aspect, the present application provides a primer composition as described in the first aspect, a kit as described in the second aspect, or an analysis method as described in the third aspect for analyzing and classifying intestinal flora.

In a fifth aspect, the present application provides an analysis method as described in the third aspect for immunohistochemical analysis.

In a sixth aspect, the present application provides a primer composition as described in the first aspect, a kit as described in the second aspect, or an analysis method as described in the third aspect for cancer diagnosis.

Preferably, the cancer is selected from, but not limited to, any one of the group consisting of intestinal cancer, adenocarcinoma and bladder cancer, or a combination of at least two thereof.

Compared with the prior art, the present application has the following beneficial effects:

(1) In the present application, by obtaining a sequencing library through two-step amplification, the primer composition can mix more samples to a greater extent, which increases the coverage of the amplified fragments, the detection specificity and sensitivity, increases the complexity of sequences in the library, reduces the proportion of phix, ensures higher sequencing quality, and reduces PCR amplification bias, and more abundant microbiome information can be obtained in combination with data analysis.

(2) The data processing and analysis method provided by the present application achieves the identification of more microbial species at taxonomic genus and species level and diversity analysis thereof and obtains relative abundance values of related microbial populations.

(3) The method for sequencing intestinal microorganisms and data analysis provided by the present application achieves the identification of more species at taxonomic genus and even species level. That is to say, more biological information about intestinal microorganisms is obtained, so that some guidance can be provided for immunohistochemical research and clinical medication.

(4) The method of the present application can be used for detecting cancer with a detection rate of more than 90%. Specifically, the detection rate for intestinal cancer can be up to 93.65% and for adenoma up to 91.53%.

DETAILED DESCRIPTION

The present application will be further described in detail below with reference to the accompanying drawings and embodiments. It is understood that the specific embodiments described herein are merely illustrative of the present application rather than limitations thereto. In addition, it should be noted that, only some but not all of the structures related to the present application are shown in the drawings for the convenience of description.

Example 1 Preparation of a Detection Kit (1) Preparation of a primer composition The first forward primer has the nucleic acid sequence as shown in SEQ ID NO. 1, and the first reverse primer has the nucleic acid sequence as shown in SEQ ID NO. 2. The nucleic acid sequences are listed as follows.

The first forward primer (SEQ ID NO. 1):
TCGTCGGCAGCGTCAGATGTGTATAAGAGACAGNNTGCCTACGGRRBG

CASCAGKVRVGAAT;

the first reverse primer (SEQ ID NO. 2):
GTCTCGTGGGCTCGGAGATGTGTATAAGAGACAGNNGGGGACTACNV

GGGTWTCTAATCC;

wherein N represents any one of bases A\T\G\C.

The P5-end adaptor sequence has the nucleic acid sequence as shown in SEQ ID NO. 3-12 which are listed as follows.

|  | Sequence | Adaptor name |
|---|---|---|
| SEQ ID NO. 3 | CTCTCTAT | S502 |
| SEQ ID NO. 4 | TATCCTCT | S503 |
| SEQ ID NO. 5 | GTAAGGAG | S505 |
| SEQ ID NO. 6 | ACTGCATA | S506 |
| SEQ ID NO. 7 | AAGGAGTA | S507 |
| SEQ ID NO. 8 | CTAAGCCT | S508 |
| SEQ ID NO. 9 | CGTCTAAT | S510 |
| SEQ ID NO. 10 | TCTCTCCG | S511 |
| SEQ ID NO. 11 | TCGACTAG | S513 |
| SEQ ID NO. 12 | TTCTAGCT | S515 |

The P7-end adaptor sequence has the nucleic acid sequence as shown in SEQ ID NO. 13-22 which are listed as follows.

|  | Sequence | Adaptor name |
|---|---|---|
| SEQ ID NO. 13 | TCGCCTTA | N701 |
| SEQ ID NO. 14 | CTAGTACG | N702 |
| SEQ ID NO. 15 | TTCTGCCT | N703 |
| SEQ ID NO. 16 | GCTCAGGA | N704 |
| SEQ ID NO. 17 | AGGAGTCC | N705 |
| SEQ ID NO. 18 | CATGCCTA | N706 |

-continued

|  | Sequence | Adaptor name |
|---|---|---|
| SEQ ID NO. 19 | GTAGAGAG | N707 |
| SEQ ID NO. 20 | CAGCCTCG | N710 |
| SEQ ID NO. 21 | TGCCTCTT | N711 |
| SEQ ID NO. 22 | TCCTCTAC | N712 |

The first tag sequence of the second forward primer is as shown in SEQ ID NO. 23 which is listed as follows.

```
The first tag sequence (SEQ ID NO. 23):
AATGATACGGCGACCACCGAGATCTACAC.
```

The partial sequence of the first universal sequencing primer of the second forward primer is as shown in SEQ ID NO. 24 which is listed as follows.
The partial sequence of the first universal sequencing primer (SEQ ID NO. 24): TCGTCGGCAGCGTC.
The tag sequence of the second reverse primer is as shown in SEQ ID NO. 25 which is listed as follows.

```
The second tag sequence (SEQ ID NO. 25):
CAAGCAGAAGACGGCATACGAGAT.
```

The partial sequence of the second universal sequencing primer of the second reverse primer is as shown in SEQ ID NO. 26 which is listed as follows.
The partial sequence of the second universal sequencing primer (SEQ ID NO. 26): GTCTCGTGGGCTCGG.
The second forward primer was AATGATACGGCGAC-CACCGAGATCTACAC-CTCTCTAT-TCGTCGGCAGCGTC
The second reverse primer was CAAGCAGAAGACGG-CATACGAGAT-TCGCCTTA-GTCTCGTGGGCTCGG.

(2) Preparation of other reagents
Buffer A: 0.5 M Tris-Cl buffer (pH 8.0), 1.0 M NaCl;
Lysis buffer B: 1 M Tris-Cl buffer (pH 8.0), 0.2 M EDTA, 10% SDS, 12% Tween-40®.
Suspension buffer C: 30 mg/ml RNAaseA
Remover D: 1.0 M $Al_2(SO_4)_3$, 250 g/L CTAB, 1.5 M NaCl;
Binding buffer E: 0.5 M Tris-Cl buffer (pH 8.0), 5 M guanidine isothiocyanate;
Rinsing buffer F: 5 M Tris-Cl buffer (pH 8.0), 25% (by volume) absolute ethanol;
Eluent G: sterile deionized water
(3) Kit assembly
The primer composition and detection probes were assembled with reagents related to the kit to prepare a detection kit.

Example 2 Extraction of Sample DNA

Three stool samples A, B and C were selected and divided into 2 equal parts, marked as: A1/A2, B1/B2 and C1/C2. A1, B1 and C1 were processed with the method described herein to obtain data. A2, B2 and C2 were sent directly to GENEWIZ for sequencing. The specific DNA extraction method included the following steps:
(1) 700-800 µl of buffer A and 250 mg of glass beads were added to a 2 ml centrifuge tube;
(2) 250 mg of sample was added to the above 2 ml centrifuge tube and vortexed for 10 s;
(3) 70 µl of lysis buffer B was added to the sample, vortexed for 7 min to mix the sample, and centrifuged at 12,000 rpm (~13,400×g) for 60 s. The supernatant (500 µl) was transferred to a new 2 ml centrifuge tube;
(4) 250 µl of suspension buffer C was added, vortexed for 10 s, allowed to stand at room temperature for 2 min, and centrifuged at 12,000 rpm (~13,400×g) for 60 s to precipitate sample particles;
(5) The supernatant was transferred to a new 2 ml centrifuge tube, 300 µl of remover D was added and mixed, and left at 4° C. for 2-5 minutes;
(6) centrifuged at 12,000 rpm (~13,400×g) for 60 s. The supernatant was transferred to a new 2 ml centrifuge tube, 1000 µl of binding buffer E was added and mixed by inverting;
(7) 700 µl of the solution obtained in the previous step was added to an adsorption column (placed in a collection tube) and centrifuged at 12,000 rpm (~13,400×g) for 30 s. The waste liquid was discarded, and then the adsorption column was placed into the collection tube;
(8) 700 µl of rinsing buffer F was added to the adsorption column and centrifuged at 12,000 rpm (~13,400×g) for 30 s. The waste liquid was discarded, and then the adsorption column was placed into the collection tube;
(9) 500 µl of 75% absolute ethanol was added to the adsorption column and centrifuged at 12,000 rpm (~13,400×g) for 30 s. The waste liquid was discarded, and then the adsorption column was placed into the collection tube;
(10) The adsorption column was placed back into the empty collection tube, centrifuged at 12,000 rpm (~13,400×g) for 60 s, and the rinsing buffer was removed as much as possible to prevent the residual ethanol in the rinsing buffer from inhibiting downstream reactions;
(11) The adsorption column was taken out and placed into a clean centrifuge tube. 50~100 µl of eluent G (the eluent can be pre-heated in water bath at 60~70° C.) was added in the middle of the adsorption membrane, allowed to stand at room temperature for 2 min, and centrifuged at 12,000 rpm (~13,400×g) for 60 s. The obtained solution was added to the centrifuge adsorption column, allowed to stand at room temperature for 2 min, and centrifuged at 12,000 rpm (~13,400×g) for 1 min;
(12) Samples were accurately quantified by using a spectrophotometer or Qubit. The DNA can be stored at 0~10° C. If stored for a long time, it can be placed at −20° C.
The extracted DNA was subjected to a purity test. The ratio of $OD_{260}/OD_{280}$ was between 1.7 and 1.9, indicating that the DNA can be directly used for the subsequent PCR and library construction.

Comparative Example 1

The lysis buffer B contained no Tween-40®, and the other components were the same as that in Example 1 and the DNA extraction method was the same as that in Example 2.
The extracted DNA was subjected to a purity test. The results showed that the ratio of $OD_{260}/OD_{280}$ was between 1.3 and 1.6, indicating that the purity was lower than that of Example 2.

Comparative Example 2

The lysis buffer B contained no $Al_2(SO_4)_3$, and the other components were the same as that in Example 1 and the DNA extraction method was the same as that in Example 2.

The extracted DNA was subjected to a purity test. The results showed that the ratio of $OD_{260}/OD_{280}$ was between 1.3 and 1.6, indicating that the purity was lower than that of Example 2.

Comparative Example 3

The lysis buffer B contained no CTAB, and the other components were the same as that in Example 1 and the DNA extraction method was the same as that in Example 2.

The extracted DNA was subjected to a purity test. The results showed that the ratio of $OD_{260}/OD_{280}$ was between 1.3 and 1.6, indicating that the purity was lower than that of Example 2.

Example 3 Library Construction (1) The reaction solution described below was prepared on ice. Except for $H_2O$ and the extracted DNA solution, a premixed amplification Mix was prepared with the following components in an amount of the reaction number+α. The prepared premixed Mix was dispensed into PCR reaction tubes. The reaction system was as follows:

| Agent | Volume |
| --- | --- |
| 2× PCR Mix ($Mg^{2+}$, dNTPs) | 12.5 μl |
| Upstream primer (1 μM) | 5 μl |
| Downstream primer (1 μM) | 5 μl |
| Sample DNA 5 ng/μl (or dd$H_2O$) | 2.5 μl |
| Total | 25 μl |

A negative control group using water as a sample was set up.

The reaction conditions were as follows:

| | Reaction procedure | Number of cycles |
| --- | --- | --- |
| Amplification procedure | 95° C. 3 min | 1 |
| | 95° C. 30 s | 28 |
| | 53° C. 30 s | |
| | 72° C. 30 s | |
| | 72° C. 5 min | 1 |

(2) Purification of the product of the first round of PCR

The product of the first round of PCR amplification was purified by using Agencourt AMPure XP (Beckman Coulter Corp.) with the specific steps of:

1) Agencourt AMPure XP magnetic beads were taken from the 4° C. refrigerator, allowed to stand at room temperature for 25 min, fully dispersed and mixed;

2) The amplification product was bound to Agencourt AMPure XP magnetic beads, wherein the volume ratio of the amplification product to Agencourt AMPure XP magnetic beads was 5:4;

3) Mixed well, then the mixture was incubated at room temperature for 15 min, centrifuged instantaneously, left on a magnetic stand for 5 min, and then the supernatant was discarded;

4) The first washing: the reaction tube was hold on the magnetic stand, 200 μl of fresh 80% ethanol was added, allowed to stand at room temperature (>30 s), and then the 80% ethanol was removed;

5) The second washing: operations of the first washing in step 4) as described above were repeated once, and the mixture was centrifuged gently to remove residual 80% ethanol;

6) Magnetic bead drying: dried at room temperature for 1 min;

7) Elution: 30 μl of eluent was added, gently pipetted up and down to mix well, then the mixture was incubated at room temperature for 15 min, centrifuged instantaneously, left on the magnetic stand for 5 min, and then the supernatant was recovered;

(3) Determination of fragment size

The amplification was identified by agarose electrophoresis, wherein the amplified product was about 550 bp in length.

(4) The second round of PCR

PCR was performed by using the PCR product obtained after purification in step (2) as a template to introduce sequencing adaptors. The specific steps were as follows:

1) The reaction solution described below was prepared on ice. Except for the purified product obtained in the first round of PCR, a premixed amplification Mix was prepared with the following components in an amount of the reaction number+α. The prepared premixed Mix was dispensed into PCR reaction tubes. The reaction system was as follows:

| Agent | Volume |
| --- | --- |
| 2× PCR Mix ($Mg^{2+}$, dNTPs) | 12.5 μl |
| Upstream primer (1 μM) | 5 μl |
| Downstream primer (1 μM) | 5 μl |
| DNA (the purified product obtained in the first round of PCR) | 2.5 μl |
| Total | 25 μl |

A negative control group using water as a sample was set up.

The reaction conditions were as follows:

| | Reaction procedure | Number of cycles |
| --- | --- | --- |
| Amplification procedure | 95° C. 3 min | 1 |
| | 95° C. 30 s | 8 |
| | 55.5° C. 30 s | |
| | 72° C. 30 s | |
| | 72° C. 5 min | 1 |

(5) Purification of the product of the second round of PCR amplification

The specific steps were the same as the purification of product of the first round of PCR, i.e., step (2), wherein the volume ratio of the PCR product to the Agencourt AMPure XP magnetic beads was 2:1;

(6) Determination of fragment size and concentration

The amplification was identified by agarose electrophoresis, wherein the amplified product was about 600 bp in length.

(7) The concentration of the PCR product was determined by using a Qubit dsDNA HS Assay Kit (Thermo Fisher) or the like;

(8) The constructed library was sequenced by Illumina MiSeq® sequencing, and the sequencing strategy was PE300 sequencing.

Example 4 Data Analysis (1) Quality control of the raw data obtained by sequencing: high-quality data was screened by information such as Barcode and primers, wherein the screening criteria was as follows: a complete sequence is comprised; a complete forward primer sequence is comprised; Barcode, primers and adaptors are removed, the sequence length must be greater than 400 bp, and no ambiguous bases are comprised; no single-base repeats in a length of more than 20 bases. The resulting sequences were respectively corresponded to each sample according to the information.

(2) Aligned with a database alignment tool and then the sequences were clustered to generate OUTs.

Figure 1:
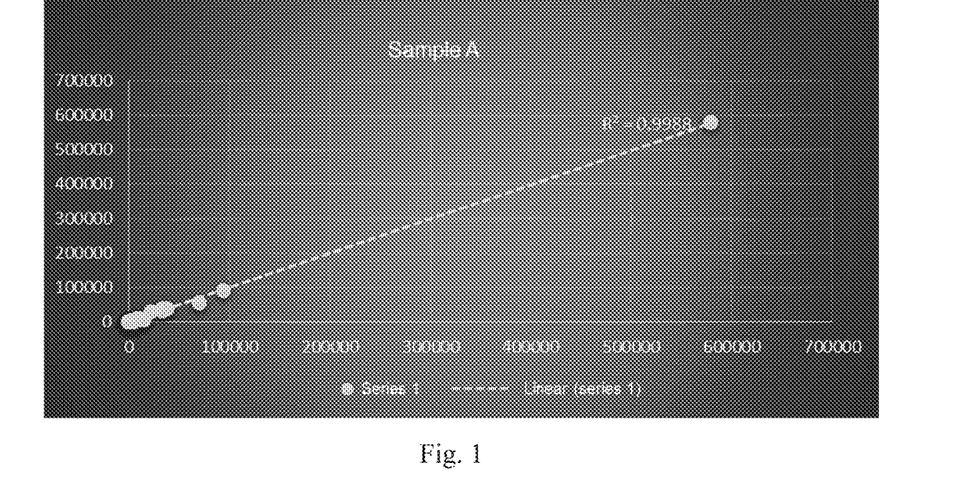
FIG. 1 is a graph showing the results of correlation analysis of sample A after data analysis in an example of the present application.
Figure 2:
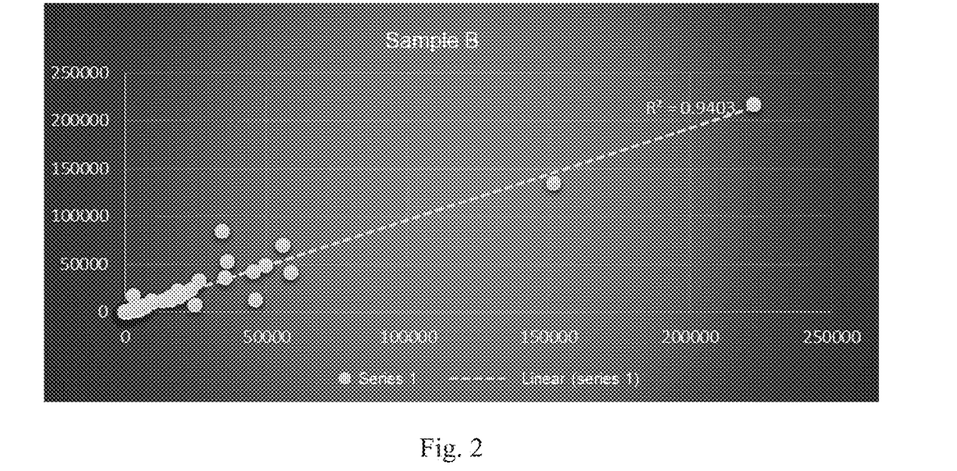
FIG. 2 is a graph showing the results of correlation analysis of sample B after data analysis in an example of the present application.
Figure 3:
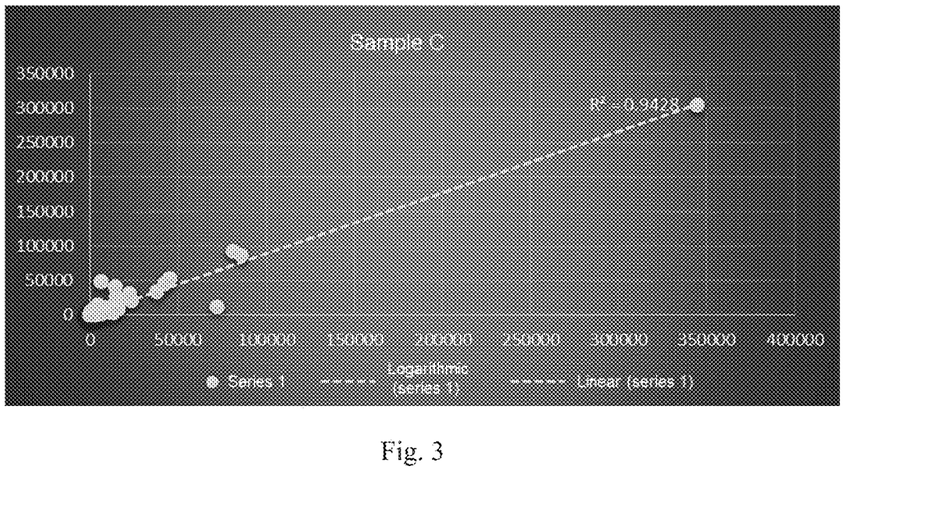
FIG. 3 is a graph showing the results of correlation analysis of sample C after data analysis in an example of the present application.

(3) The obtained OTUs were subjected to correlation analysis according to A1/A2, B1/B2 and C1/C2. The results were shown in FIGS. 1-3.

The sample A was divided to two parts, which were then used for library construction and sequencing respectively by using the method provided herein and the method provided by GENEWIZ. The obtained data were subjected to analysis followed by correlation analysis. It can be seen from FIG. 1 that the correlation between the OTUs obtained by the two methods reached 0.9988. The sample B was divided to two parts, which were then used for library construction and sequencing respectively by using the method provided herein and the method provided by GENEWIZ. The obtained data were subjected to analysis followed by correlation analysis. It can be seen from FIG. 2 that the correlation between the OTUs obtained by the two methods reached 0.9403. The sample C was divided to two parts, which were then used for library construction and sequencing respectively by using the method provided herein and the method provided by GENEWIZ. The obtained data were subjected to analysis followed by correlation analysis. It can be seen from FIG. 3 that the correlation between the OTUs obtained by the two methods reached 0.9428.

Example 5 Analysis Verification

Stool samples from 63 patients with intestinal cancer, stool samples from 59 patients with adenoma and stool samples from 66 healthy patients were subjected to extraction, library construction and sequencing by using the method of the present patent to obtain DNA sequence information. The risk of intestinal cancer was predicted according to the sequence information, wherein the specific test method was the same as that in Example 2-Example 4. The results were shown in Table 1.

TABLE 1

|  | Intestinal cancer | Adenoma | Healthy person |
|---|---|---|---|
| Actual number | 63 | 59 | 66 |
| Number of intestinal cancer detected | 59 | 5 | 0 |
| Number of adenomas detected | 4 | 54 | 8 |
| Number of healthy detected | 0 | 0 | 58 |
| Accuracy | 93.65% | 91.53% | 87.88% |

As can be seen from Table 1, in the detection of the present application, the detection rate for intestinal cancer was 93.65%, the detection rate for adenoma was 91.53% and the accuracy for healthy person was 87.88%. It can be seen that the accuracy of the method of the present application for detecting cancer can reach more than 90%.

In summary, in the present application, by obtaining a sequencing library through two-step amplification, the primer composition can mix more samples to a greater extent, which increases the coverage of the amplified fragments, the detection specificity and sensitivity, increases the complexity of sequences in the library, reduces the proportion of phix, ensures higher sequencing quality, and reduces PCR amplification bias, and more abundant microbiome information can be obtained in combination with data analysis. The data processing and analysis method provided by the present application achieves the identification of more microbial species at taxonomic genus and species level and diversity analysis thereof and obtains relative abundance values of related microbial populations.

It should be noted that the above examples are only preferred embodiments of the present application and technical principles applied thereto. A person skilled in the art will understand that the present application is not limited to the specific embodiments described herein, and that various changes, modifications and substitutions can be made by those skilled in the art without departing from the scope of the invention. Therefore, although the present application has been described in detail by the above embodiments, the present application is not limited to the above embodiments, and other equivalent embodiments may be included without departing from the concept of the present application. The scope of the present application is determined by the scope of the appended claims.

The invention claimed is:

1. A primer composition for analyzing intestinal flora comprising:
a first set of primers, which comprises a first forward primer and a first reverse primer, wherein the first forward primer includes the following four consecutive portions from 5'- to 3'-end: a first universal sequencing primer, a 2-bp random base sequence, a linker sequence and an intestinal flora 16S rRNA V3-V4 region-specific forward primer; the first reverse primer includes the following four consecutive portions from 5'- to 3'-end: a second universal sequencing primer, a 2-bp random base sequence, a linker sequence and an intestinal flora 16S rRNA V3-V4 region-specific reverse primer;

a second set of primers, which comprises a second forward primer and a second reverse primer, wherein the second forward primer includes the following three consecutive portions from 5'- to 3'-end: a P5-end adaptor sequence, a first tag sequence and partial sequence of the first universal sequencing primer; the second reverse primer includes the following three consecutive portions from 5'- to 3'-end: a P7-end adaptor sequence, a second tag sequence and partial sequence of the second universal sequencing primer, wherein the first forward primer has the nucleic acid sequence as shown in SEQ ID NO. 1, and the first reverse primer has the nucleic acid sequence as shown in SEQ ID NO. 2; the P5-end adaptor sequence has the nucleic acid sequence as shown in SEQ ID NO. 3-12; the P7-end adaptor sequence has the nucleic acid sequence as shown in SEQ ID NO. 13-22; the first tag sequence of the second forward primer is as shown in SEQ ID NO. 23; the partial sequence of the first universal sequencing primer of the second forward primer is as shown in SEQ ID NO. 24; the second tag sequence of the second reverse primer is as shown in SEQ ID NO. 25; and the partial sequence of the second universal sequencing primer of the second reverse primer is as shown in SEQ ID NO. 26.

2. A kit for analyzing intestinal flora comprising the primer composition according to claim 1.

3. A method for analyzing intestinal flora by using the primer composition according to claim 1, comprising the steps of
   a) extraction of genomic DNA from a sample;
   b) construction of an amplicon library: performing two rounds of PCR amplification to construct a high-throughput sequencing library, wherein the first set of primers is used in the first round of PCR amplification and the second set of primers is used in the second round of PCR amplification;
   c) data analysis: performing sequencing to obtain sequencing reads differentiated by tags, assembling according to the overlap relationship of the reads to obtain full-length sequences of the high variable region V3-V4, and then classifying and analyzing the full-length sequences to obtain a classification of the microbial population; wherein the step of classifying and analyzing of the full-length sequences specifically includes the steps of calculating the diversity of the full-length sequences, performing operational taxonomy unit (OTU) classification according to the sequence diversity, assigning the full-length sequences to OTUs, then aligning the full-length sequences in each OTU classification to the V6 database of 16S rRNA and annotating the OTUs at species level by using the alignment results according to the mode principle.

4. The method according to claim 3, wherein the extraction of genomic DNA from a sample in step a) comprises the specific steps of
   a') mixing the sample with a lysis buffer, and then resuspending;
   b') adding a remover into the resuspended sample obtained in step a'), mixing and centrifuging;
   c') adding a binding buffer into the centrifuged sample obtained in step b') and mixing, adding the mixture into an adsorption column, centrifuging, rinsing, adding 75% absolute ethanol, and centrifuging;
   d') adding an eluent into the centrifuged sample obtained in step c') and centrifuging to obtain genomic DNA.

5. The method according to claim 4, wherein the remover in step b') comprises $Al_2(SO_4)_3$, CTAB and NaCl.

6. The method according to claim 5, wherein the molar concentration of the $Al_2(SO_4)_3$ is 0.5-2 M;
   the mass concentration of the CTAB is 200-300 g/L; and
   the molar concentration of the NaCl is 0.8-2 M.

7. The method according claim 3, wherein the conditions for the first round of PCR as described in step b) are: pre-denaturation at 93-96° C. for 1-5 min; 25-35 cycles of pre-denaturation at 93-96° C. for 20-40 s, 50-55° C. for 20-40 s, and 70-75° C. for 20-40 s; and extension at 70-75° C. for 3-6 min; and
   the conditions for the second round of PCR as described in step b) are: pre-denaturation at 93-96° C. for 1-5 min; 6-12 cycles of pre-denaturation at 93-96° C. for 20-40 s, 54-58° C. for 20-40 s, and 70-75° C. for 20-40 s; and extension at 70-75° C. for 3-6 min.

8. The method according to claim 3, wherein the sample in step a) is derived from any one of the group consisting of feces, soil, urine and oral cells, or a combination of at least two thereof.

9. The method according to claim 3, wherein a purification step is further included after step a).

10. The method according to claim 9, wherein the purification is performed by using magnetic beads;
    wherein the volume ratio of the magnetic beads to the amplification product is (0.4-0.7): 1.

11. A method for diagnosing cancer with the primer composition according to claim 1, comprising:
    a) extraction of genomic DNA from a sample;
    b) construction of an amplicon library: performing two rounds of PCR amplification to construct a high-throughput sequencing library, wherein the first set of primers is used in the first round of PCR amplification and the second set of primers is used in the second round of PCR amplification
    c) performing sequencing to obtain DNA sequence information; and
    d) predicting cancer according to the sequence information.

12. The method according to claim 11, wherein the cancer is any one of the group consisting of intestinal cancer, adenocarcinoma and bladder cancer, or a combination of at least two thereof.

* * * * *

SEQUENCE LISTING

```
<160> NUMBER OF SEQ ID NOS: 26

<210> SEQ ID NO 1
<211> LENGTH: 62
<212> TYPE: DNA
<213> ORGANISM: Artificial sequence
<220> FEATURE:
<223> OTHER INFORMATION: synthetic first forward primer
<220> FEATURE:
<221> NAME/KEY: misc_feature
<222> LOCATION: (34)..(35)
<223> OTHER INFORMATION: n is a, c, g, or t

<400> SEQUENCE: 1
tcgtcggcag cgtcagatgt gtataagaga cagnntgcct acggrrbgca scagkvrvga    60
at                                                                  62
```

```
<210> SEQ ID NO 2
<211> LENGTH: 60
<212> TYPE: DNA
<213> ORGANISM: Artificial sequence
<220> FEATURE:
<223> OTHER INFORMATION: synthetic first reverse primer
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 2
gtctcgtggg ctcggagatg tgtataagag acagnngggg actacnvggg twtctaatcc    60

<210> SEQ ID NO 3
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 3 ctctctat                                                              8

<210> SEQ ID NO 4
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 4 tatcctct                                                              8

<210> SEQ ID NO 5
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 5 gtaaggag                                                              8

<210> SEQ ID NO 6
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 6 actgcata                                                              8

<210> SEQ ID NO 7
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 7 aaggagta                                                              8
```

-continued

```
<210> SEQ ID NO 8
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 8 ctaagcct                                                                 8

<210> SEQ ID NO 9
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 9 cgtctaat                                                                 8

<210> SEQ ID NO 10
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 10 tctctccg                                                                 8

<210> SEQ ID NO 11
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 11 tcgactag                                                                 8

<210> SEQ ID NO 12
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 12 ttctagct                                                                 8

<210> SEQ ID NO 13
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 13 tcgcctta                                                                 8

<210> SEQ ID NO 14
<211> LENGTH: 8
<212> TYPE: DNA
<213> ORGANISM: Artificial sequence
<220> FEATURE:
<223> OTHER INFORMATION: Synthetic oligonucleotide
```

```
<400> SEQUENCE: 14 ctagtacg                                                                    8

<210> SEQ ID NO 15
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 15 ttctgcct                                                                    8

<210> SEQ ID NO 16
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 16 gctcagga                                                                    8

<210> SEQ ID NO 17
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 17 aggagtcc                                                                    8

<210> SEQ ID NO 18
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 18 catgccta                                                                    8

<210> SEQ ID NO 19
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 19 gtagagag                                                                    8

<210> SEQ ID NO 20
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 20 cagcctcg                                                                    8

<210> SEQ ID NO 21
```

```
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 21 tgcctctt                                                          8

<210> SEQ ID NO 22
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 22 tcctctac                                                          8

<210> SEQ ID NO 23
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 23
atgatacggc gaccaccgag atctacac                                    28

<210> SEQ ID NO 24
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 24
tcgtcggcag cgtc                                                   14

<210> SEQ ID NO 25
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 25
caagcagaag acggcatacg agat                                        24

<210> SEQ ID NO 26
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 26
gtctcgtggg ctcgg                                                  15
```